US009339025B2

(12) United States Patent
Yoshida et al.

(10) Patent No.: US 9,339,025 B2
(45) Date of Patent: May 17, 2016

(54) METHOD FOR ENHANCING RED BLOOD CELL QUALITY AND SURVIVAL DURING STORAGE

(75) Inventors: Tatsuro Yoshida, West Newton, MA (US); Larry J. Dumont, Lebanon, NH (US)

(73) Assignees: New Health Sciences, Inc., Bethesda, MD (US); Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/218,114

(22) Filed: Aug. 25, 2011

(65) Prior Publication Data

US 2012/0225416 A1 Sep. 6, 2012

Related U.S. Application Data

(60) Provisional application No. 61/376,899, filed on Aug. 25, 2010.

(51) Int. Cl.
*A01N 1/02* (2006.01)
*A61M 1/02* (2006.01)

(52) U.S. Cl.
CPC .............. *A01N 1/021* (2013.01); *A01N 1/0242* (2013.01); *A61M 1/0272* (2013.01)

(58) Field of Classification Search
None
See application file for complete search history.

(56) References Cited

U.S. PATENT DOCUMENTS

| 4,086,924 A | 5/1978 | Latham, Jr. |
| 4,228,032 A * | 10/1980 | Talcott ............... 252/400.31 |
| 4,300,559 A | 11/1981 | Gajewski et al. |
| 4,370,160 A | 1/1983 | Ziemelis |
| 4,381,775 A | 5/1983 | Nose' et al. |
| 4,540,416 A | 9/1985 | Hattori et al. |
| 4,572,899 A | 2/1986 | Walker et al. |
| 4,585,735 A | 4/1986 | Meryman et al. |
| 4,629,544 A | 12/1986 | Bonaventura et al. |
| 4,654,053 A | 3/1987 | Sievers et al. |
| 4,670,013 A | 6/1987 | Barnes et al. |
| 4,701,267 A | 10/1987 | Watanabe et al. |
| 4,713,176 A | 12/1987 | Schoendorfer et al. |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,837,047 A * | 6/1989 | Sato et al. ................. 422/41 |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 5,000,848 A | 3/1991 | Hodgins et al. |
| 5,023,054 A | 6/1991 | Sato et al. |
| 5,037,419 A | 8/1991 | Valentine et al. |
| 5,152,905 A | 10/1992 | Pall et al. |
| 5,192,320 A | 3/1993 | Anazawa et al. |
| 5,208,335 A | 5/1993 | Ramprasad et al. |
| 5,229,012 A | 7/1993 | Pall et al. |
| 5,254,248 A | 10/1993 | Nakamura et al. |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,476,764 A | 12/1995 | Bitensky |
| 5,506,141 A | 4/1996 | Weinreb et al. |
| 5,529,821 A | 6/1996 | Ishikawa et al. |
| 5,617,873 A | 4/1997 | Yost et al. |
| 5,624,794 A | 4/1997 | Bitensky et al. |
| 5,635,358 A | 6/1997 | Wilding et al. |
| 5,691,452 A | 11/1997 | Gawryl et al. |
| 5,693,230 A | 12/1997 | Asher |
| 5,698,250 A | 12/1997 | DelDuca et al. |
| 5,730,989 A | 3/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,811,142 A | 9/1998 | DelDuca et al. |
| 5,846,427 A | 12/1998 | Kessler et al. |
| 5,902,747 A | 5/1999 | Nemser et al. |
| 5,972,710 A | 10/1999 | Weigl et al. |
| 6,027,623 A | 2/2000 | Ohkawa |
| 6,045,701 A | 4/2000 | Ung-Chhun et al. |
| 6,047,203 A | 4/2000 | Sackner et al. |

(Continued)

FOREIGN PATENT DOCUMENTS

| CN | 2894710 Y | 5/2007 |
| DE | 3722984 | 1/1989 |

(Continued)

OTHER PUBLICATIONS

Yoshida et al, Extended storage of red blood cells under anaerobic conditions, 2007, Vox Sanguinis 92, 22-31.*
Sigma-Aldrich Product Specification, Citrate-dextrose solution (ACD).*
International Search Report and Written Opinion dated Jan. 18, 2012 corresponding to international patent application PCT/US11/49168.
Alcantar et al., "Polyethylene glycol-coated biocompatible surfaces," *Journal of Biomedical Materials Research*, 51(3):343-351 (2000).

(Continued)

*Primary Examiner* — Sharmila G. Landau
*Assistant Examiner* — Stephanie McNeil
(74) *Attorney, Agent, or Firm* — Arnold & Porter LLP

(57) ABSTRACT

The present invention is a method for enhancing the quality and survival of red blood cells during storage by depleting the red blood cells of both carbon dioxide and oxygen and maintaining 2,3-diphosphoglycerate acid levels.

17 Claims, No Drawings

(56) References Cited

U.S. PATENT DOCUMENTS

| | | |
|---|---|---|
| 6,090,062 A | 7/2000 | Sood et al. |
| 6,150,085 A | 11/2000 | Hess et al. |
| 6,156,231 A | 12/2000 | McKedy |
| 6,162,396 A * | 12/2000 | Bitensky et al. ............... 422/44 |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,482,585 B2 | 11/2002 | Dottori |
| 6,527,957 B1 | 3/2003 | Deniega et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,723,051 B2 | 4/2004 | Davidson et al. |
| 6,761,695 B2 | 7/2004 | Yost et al. |
| 6,773,407 B2 | 8/2004 | Yost et al. |
| 6,817,979 B2 | 11/2004 | Nihtilä |
| 6,866,783 B2 | 3/2005 | Baurmeister et al. |
| 6,899,822 B2 | 5/2005 | McKedy |
| 6,955,648 B2 | 10/2005 | Mozayeni et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,775,376 B2 | 8/2010 | Bonaguidi et al. |
| 8,071,282 B2 | 12/2011 | Bitensky et al. |
| 2001/0027156 A1 | 10/2001 | Egozy et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0182241 A1 | 12/2002 | Borenstein et al. |
| 2003/0003575 A1 | 1/2003 | Vacanti et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2004/0026341 A1 | 2/2004 | Hogberg et al. |
| 2004/0126880 A1 | 7/2004 | Manders et al. |
| 2004/0168982 A1 | 9/2004 | Bitensky et al. |
| 2005/0038342 A1 | 2/2005 | Mozayeni et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2007/0078113 A1 | 4/2007 | Roth et al. |
| 2007/0240569 A1 | 10/2007 | Ooya |
| 2008/0160107 A1 | 7/2008 | McCaney et al. |
| 2008/0243045 A1 | 10/2008 | Pasqualini |
| 2009/0017128 A1 | 1/2009 | Monzyk et al. |
| 2009/0269837 A1 | 10/2009 | Shevkoplyas et al. |
| 2010/0133203 A1 | 6/2010 | Walker et al. |
| 2010/0221697 A1 | 9/2010 | Sehgal |
| 2010/0313755 A1 | 12/2010 | Koros et al. |
| 2012/0024156 A1 | 2/2012 | Yoshida et al. |
| 2012/0077182 A1 | 3/2012 | Bitensky et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0219633 A1 | 8/2012 | Sowemimo-Coker |
| 2013/0004937 A1 | 1/2013 | Yoshida et al. |
| 2013/0327677 A1 | 12/2013 | McDorman |

FOREIGN PATENT DOCUMENTS

| | | |
|---|---|---|
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 109 447 B1 | 10/2003 |
| FR | 2 581 289 A1 | 11/1986 |
| GB | 1 044 649 A2 | 10/1966 |
| JP | 58-194879 | 11/1983 |
| JP | 63-63616 A | 3/1988 |
| JP | 01-104271 A | 4/1989 |
| JP | 5-503075 A | 5/1993 |
| JP | 5-503304 A | 6/1993 |
| JP | H05-148151 A | 6/1993 |
| JP | 5-305123 A | 11/1993 |
| JP | H05-305123 A | 11/1993 |
| JP | 06-121920 A | 5/1994 |
| JP | 2700170 B2 | 1/1998 |
| JP | 2000-516963 A | 12/2000 |
| JP | 2002-253936 A | 9/2002 |
| JP | 2004/089495 | 3/2004 |
| JP | 2005-533041 A | 11/2005 |
| JP | 2005-535279 A | 11/2005 |
| JP | 2006-502078 A | 1/2006 |
| JP | 2007-260393 A | 10/2007 |
| JP | 10/501443 | 2/2010 |
| JP | 2010-503501 A | 2/2010 |
| KR | 10-0721054 | 5/2006 |
| SU | 1718766 A1 | 1/1990 |
| WO | WO 81/02239 A1 | 8/1981 |
| WO | WO 86/00809 A1 | 2/1986 |
| WO | 89/02274 | 3/1989 |
| WO | WO 91/04659 A1 | 4/1991 |
| WO | WO 92/08348 A1 | 5/1992 |
| WO | WO 95/29662 A2 | 11/1995 |
| WO | WO 96/29103 | 9/1996 |
| WO | WO 96/29346 | 9/1996 |
| WO | WO 96/29864 A1 | 10/1996 |
| WO | WO 97/37628 A1 | 10/1997 |
| WO | WO 98/51147 A1 | 11/1998 |
| WO | WO 99/48963 A2 | 9/1999 |
| WO | WO 03/043419 A1 | 5/2003 |
| WO | WO 03/043571 A2 | 5/2003 |
| WO | WO 03/086577 A1 | 10/2003 |
| WO | WO 2006/057473 A1 | 6/2006 |
| WO | WO 2011/014855 | 2/2011 |
| WO | WO 2011/046841 A1 | 4/2011 |
| WO | WO 2012/061731 A1 | 5/2012 |

OTHER PUBLICATIONS

Anderson et al., "Microfabrication and microfluidics for tissue engineering: state of the art and future opportunities," *Lab Chip*, 4:98-103 (2004).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

(56) References Cited

OTHER PUBLICATIONS

Bardy et al., "Technetium-99m Labeling by Means of Stannous Pyrophosphate: Application to Bleomycin and Red Blood Cells," *Journal of Nuclear Medicine*, 16(5):435-437 (1975).
Barras et al., "Einfluss der Rejuvenation auf die rheologischen Eigenschaften gelagerter Erythrozyten," *VASA*, 23(4):305-311 (1994) (with translation).
Beutler et al., "Storage of red cell concentrates in CPD-A2 for 42 and 49 days," *The Journal of Laboratory and Clinical Medicine*, 102(1):53-62 (1983).
Borenstein et al., "Microfabrication Technology for Vascularized Tissue Engineering," *Biomedical Microdevices*, 4(3):167-175 (2002).
Brody el al., "Deformation and Flow of Red Blood Cells in a Synthetic Lattice: Evidence for an Active Cytoskeleton," *Biophysical Journal*, 68:2224-2232 (1995).
Carmen, "The Selection of Plastic Materials for Blood Bags," *Transfusion Medicine Reviews*, 7(1):1-10 (1993).
Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on Dec. 11, 2012, from: http://www.rheoscan.com/products/products/products-01.html.
Chilton et al., "Privacy Protection of Health Information: Patient Rights and Pediatrician Responsibilities," *Pediatrics*, 104(4):973-977 (1999).
Cokelet et al., "Fabrication of in Vitro Microvascular Blood Flow Systems by Photolithography," *Microvascular Research*, 46:394-400 (1993).
Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
De Angelis et al., "Erythrocyte Shape Control in Stored Blood: The Effect of Additive Solutions on Shape Recovery," *Haematologica*, 73:7-12 (1988).
Deible et al., "Molecular barriers to biomaterial thrombosis by modification of surface proteins with polyethylene glycol," *Biomaterials*, 19:1885-1893 (1998).
De Venuto et al., "Rejuvenation of Human Red Blood Cells During Liquid Storage," *Transfusion*, 14(4):338-344 (1974).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumont et al., "Anaerobic storage of red blood cells in a novel additive solution improves in vivo recovery," *Transfusion*, 49(3):458-464 (2009).
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Fahraeus el al., "The Viscosity of the Blood in Narrow Capillary Tubes," *Am. J.Physiol.*, 96(3):562-568 (1931).
Fang et al., "Inhibition of Lipopolysaccharide-Associated Endotoxin Activities In Vitro and In Vivo by the Human Anti-Lipid a Monoclonal Antibody SdJ5-1.17.15," *Infection and Immunity*, 61(9):3873-3878 (1993).
Frame et al., "A System for Culture of Endothelial Cells in 20-50-μm Branching Tubes," *Microcirculation*, 2(4):377-385 (1995).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Hamasaki et al., "Acid-citrate-dextrose-phosphoenolpyruvate medium as a rejuvenant for blood storage," *Transfusion*, 23(1):1-7 (1983).
Hess, "Extended Liquid Storage of Red Blood Cells," Blood Donors and the Supply of Blood and Blood Products, National Academy Press, Washington, D.C., pp. 99-102 (1996).
Hess el al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen on Red Cells during Liquid Storage at +4° C," *Vox Sang.*, 51:27-34 (1986).
Högman et al., "Effects of Oxygen and Mixing on red cells stored in plastic bags at +4°C," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythroso®)," *Transfus. Sci.*, 16(2):193-199 (1995).
Huang et al., "Continuous Particle Separation Through Deterministic Lateral Displacement," *Science*, 304:987-990 (2004).
International Preliminary Report on Patentability completed on Feb. 14, 2012, in International Patent Application No. PCT/US2010/52084.
International Preliminary Report on Patentability completed on May 21, 2012, in International Patent Application No. PCT/US2010/52376.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report completed on Nov. 22, 2010, in International Patent Application No. PCT/US2010/052376.
International Search Report completed on Feb. 8, 2011, in International Patent Application No. PCT/US10/52084.
International Search Report completed on Apr. 26, 2011, in International Patent Application No. PCT/US2010/044045.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report completed on Nov. 9, 2012, in International Patent Application No. PCT/US12/45426.

(56) References Cited

OTHER PUBLICATIONS

Jain, et al., "Determinants of Leukocyte Margination in Rectangular Microchannels," *PLoS One*, 4(9):1-8 (2009).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C," *Transfusion*, 26(6):500-505 (1986).
Meryman et al., "Extending the storage of red cells at 4° C," *Transfus. Sci.*, 15(2):105-115 (1994).
Moll et al., "Dean vortices applied to membrane process. Part II: Numerical approach," *Journal of Membrane Science*, 288:321-335 (2007).
Moroff el al., "Proposed standardization of methods for determining the 24-hour survival of stored red cells," *Transfusion*, 24:109-114 (1984).
Murphy et al., "Increased Mortality, Postoperative Morbidity, and Cost After Red Blood Cell Transfusion in Patients Having Cardiac Surgery," *Circulation*, 116:2544-2552 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Poxton, "Antibodies to lipopolysaccharide," *Journal of Immunological Methods*, 186:1-15 (1995).
Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
The International Committee for Standardization in Hematology, "Recommended Methods for Radioisotope Red Cell Survival Studies," *Blood*, 38(3):378-386 (1971).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C in additive solution (AS-1, AS-3, or AS-5) for 42 days and then biochemically modified, frozen, thawed, washed, and stored at 4° C in sodium chloride and glucose solution for 24 hours," *Transfusion*, 40:1341-1345 (2000).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of Trauma*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion*, 7(6):401-408 (1967).
Wu et al., "Polymer microchips bonded by $O_{26}$-plasma activation," *Electrophoresis*, 23:782-790 (2002).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).
Burns et al., "Artificial microvascular network: a new tool for measuring rheologic properties of stored red blood cells," *Transfusion*, 52(5):1010-1023 (2012).
Gifford et al., "Parallel Microchannel-Based Measurements of Individual Erythrocyte Areas and Volumes," *Biophysical Journal*, 84:623-633 (2003).
Gifford et al., "A detailed study of time-dependent changes in human red blood cells: from reticulocyte maturation to erythrocyte senescence," *British Journal of Haematology*, 135:395-404 (2006).
Prefiltration before membrane filtration, hydrophobic, 25 μm 142 mm, retrieved on Aug. 26, 2014, from: www.emdmillipore.com/US/en/product/Prefiltration-before-membrane-filtration.

(56) References Cited

OTHER PUBLICATIONS

Durapore® Membrane Filters—Filter Discs and Membranes, retrieved on Aug. 26, 2014, from: www.emdmillipore.com/US/en/product/Durapore.

International Search Report and Written Opinion issued in International Application PCT/US2014/019537 dated Jul. 10, 2014.

Extended European Search Report, dated Aug. 8, 2014 for European patent Application No. 10823965.8.

Extended European Search Report dated Oct. 30, 2014 in European Patent Application No. 11838889.1.

Extended European Search Report dated Nov. 4, 2014 in European Patent Application No. 12807324.4.

Holme et al., "Current Issues Related to the Quality of Stored RBCs," *Transfusion and Apheresis Science*, 33(1):55-61 (2005).

Supplementary European Search Report dated Jan. 20, 2015 in European Patent Application No. 12822378.2.

Bensinger et al., "Prolonged maintenance of 2,3-DPG in liquid blood storage: Use of an internal $CO_2$ trap to stabilize pH," J. Lab. Clin. Med., 89(3):498-503, Mar. 1977.

de Korte et al., "Prolonged maintenance of 2,3-diphosphoglycerate acid and adenosine triphosphate in red blood cells during storage," *Transfusion*, 48:1081-1089, Jun. 2008.

Gulliksson et al., "Storage of whole blood overnight in different blood bags preceding preparation of blood components: in vitro effects on red blood cells," *Blood Transfus* 7:210-215, 2009.

Hess et al. "Successful storage of RBCs for 9 weeks in a new additive solution," *Transfusion*, 40:1007-1011, Aug. 2000.

Hess et al., "Alkaline CPD and the preservation of RBC 2,3-DPG," *Transfusion*, 42:747-752, Jun. 2002.

Hess et al., "Storage of Red Blood Cells: New Approaches," *Transfusion Medicine Reviews*, 16(4):283-295, Oct. 2002.

Högman, "Preparation and Preservation of Red Cells," *Vox Sanguinis* 74(Suppl. 2):177-187, 1998.

Murphy et al., "Platelet Storage at 22° C: Role of Gas Transport Across Plastic Containers in Maintenance of Viability," *Blood*, 46(2):209-218, Aug. 1975.

Extended European Search Report, dated Jun. 15, 2015, in European Patent Application No. 11820660.6.

Dumont et al., "$CO_2$-Dependent Metabolic Modulation in Red Blood Cells Stored Under Anaerobic Conditions," *Transfusion*, vol. 00, (2015).

Lowndes, "Blood Interference in fluorescence Spectrum: Experiment, analysis and comparison with intraoperative measurements on brain tumor," Bachelor Thesis, Linköping University, pp. 1-42 (2010).

* cited by examiner

METHOD FOR ENHANCING RED BLOOD CELL QUALITY AND SURVIVAL DURING STORAGE

CROSS-REFERENCE TO RELATED APPLICATIONS

The present application claims priority based on U.S. Provisional Application No. 61/376,899, filed Aug. 25, 2010, which is incorporated herein by reference in its entirety.

BACKGROUND OF THE INVENTION

1. Field of the Invention

The present invention relates to a method for enhancing red blood cell quality and survival during storage.

2. Background of the Art

Anaerobic storage of red blood cells has been shown to enhance the metabolic status of red blood cells (RBC) and an increase in the potential storage time can be achieved using a variety of additive solutions. When combining an alkaline additive solution with anaerobic storage, it was observed that storage under anaerobic conditions yields insignificant benefits in terms of ATP levels. However, when the RBC additive pH was lowered from 8.1 to 6.5, significant improvement in metabolic parameters were observed under anaerobic conditions. While it has been suggested that overalkalinization of RBCs in alkaline additive solution results in increased intracellular pH due to $CO_2$ removed during oxygen depletion, the direct effects of $CO_2$ depletion on RBC quality and storage have not been demonstrated.

SUMMARY OF THE INVENTION

The present invention is a method for enhancing red blood cell quality and survival during storage by depleting a red blood cell sample of both oxygen and carbon dioxide; and transferring the oxygen- and carbon dioxide-depleted red blood cell sample to an oxygen- and carbon dioxide-impermeable environment for storage. In one embodiment, the red blood cell sample includes acidified additive solution so that 2,3-diphosphoglyceratic acid levels are maintained. In some embodiments, the red blood cell sample is stored for at least three weeks and the red blood cells exhibit less than 0.2% hemolysis. In other embodiments, the red blood cells sample is stored for at least seven weeks and the red blood cells exhibit less than 0.3% hemolysis. In yet other embodiments, the red blood cells sample is stored for at least nine weeks and the red blood cells exhibit less than 0.7% hemolysis. The present disclosure provides for a method for enhancing red blood cell quality and survival during storage including the steps of reducing oxygen and carbon dioxide in a red blood cell sample; and storing the oxygen and carbon dioxide reduced red blood cell sample in an oxygen and carbon dioxide-impermeable storage environment. Adenosine triphosphate (ATP) and 2,3-diphosphoglycerate (2,3-DPG) levels are optimized during storage in the storage environment. The present disclosure provides for a method for enhancing red blood cell quality and survival during storage including the steps of reducing oxygen and carbon dioxide in a red blood cell sample; and storing the oxygen and carbon dioxide reduced red blood cell sample in an oxygen and carbon dioxide-impermeable storage environment. Adenosine triphosphate (ATP) and 2,3-diphosphoglycerate (2,3-DPG) levels are optimized during storage in the oxygen and carbon dioxide-impermeable storage environment.

DETAILED DESCRIPTION OF THE INVENTION

It has now been demonstrated that removal of $CO_2$ from RBC provides a metabolic advantage for the RBC by providing for an improved maintenance of 2,3-diphosphoglycerate acid (DPG) in the RBC. Prior to the present invention, it was shown that RBCs in an oxygen depleted environment (i.e., anaerobic) have better in vivo recovery kinetics in humans, better maintenance of ATP, and better maintenance of 2,3,-DPG) However, it was suggested that the maintenance of ATP levels in the oxygen depleted RBC could be explained not because of $O_2$ removal, but rather because, under the experimental conditions, there was a concomitant removal of $CO_2$ leading to alkalization (i.e., increase in pH) of the RBC that in turn has a direct effect on the enzyme phosphofructokinase, a rate limiting factor in glycolysis. It has been suggested that with an acidified additive solution under anaerobic conditions, an increase in ATP is due primarily not from the pH effect on glycolysis, but rather through the effect of the deoxygenated hemoglobin binding free 2,3-DPG, wherein alkalinization may play a secondary role in ATP maintenance in the anaerobically stored RBC. Experiments where carbon monoxide was used to displace 2,3,-DPG from the deoxygenated hemoglobin were shown to provide no improvement in ATP levels over storage (i.e., ATP was similar to oxygen stored RBC).

Based upon the above suggestions, one would expect that $CO_2$ depletion would contribute to alkalization of the RBC cytosol in addition to the alkalization effect of protons (H+) being bound by deoxygenated hemoglobin. This additional alkalization from $CO_2$ depletion would then increase the flux through glycolysis (Scheme 1) because of the effect on the phosphofructokinase enzyme and increase the production of ATP.

SCHEME 1

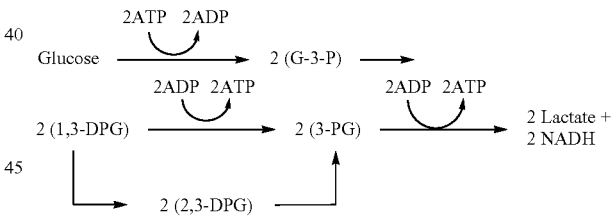

As described in Table 1, maintaining $CO_2$ when $O_2$ was depleted matched the pH of the control aerobic condition whereas $CO_2$ removal resulted in alkalinization. ATP was higher in the $CO_2$ replete anaerobic arm than the control and the $CO_2$ depleted anaerobic arm. Glycolysis rate, as indicated by lactate accumulation and glucose consumption, was equivalent in the $CO_2$ replete arm than in the control arm. Glycolysis rate was slightly greater in the $CO_2$ depleted anaerobic arm that the other two, but ATP in this arm was lower than the $CO_2$ replete arm that has a pH the same as the control arm. These observations indicate that the main ATP metabolic advantage for anaerobic storage is not through the pH affect on phosphofructokinase. Further, ATP association with hemoglobin and less ATP utilization through the pentose phosphate pathway or other pathways may be important contributors to the maintenance of ATP over storage in the anaerobic environment. However, unexpectedly, 2,3-DPG was depleted in the $CO_2$ replete anaerobic arm like the control, indicating that there is a previously undescribed effect of $CO_2$ (perhaps through pH) on diphosphoglycerate mutase and/or diphosphoglycerate phosphatase in DPG synthesis or other pathway.

TABLE 1

| | Results | Control Aerobic | Anaerobic with $CO_2$ preservation[1] | Anaerobic with $CO_2$ depletion[2] |
|---|---|---|---|---|
| Expected | Glycolysis (Lactate) | Control | Equal to control | Greater than control |
| | ATP | Control OK | Greater than control (because anaerobic) | Greater than control Perhaps slightly greater than $CO_2$ replete |
| | 2,3-DPG | Control depleted | Greater than control (because anaerobic) | Greater than control (through ~21 days) |
| Observed | Glycolysis (Lactate) | Control | Equal to control | Greater than control |
| | | Control OK | Greater than control Greater than $CO_2$ depleted** | Greater than control Less than $CO_2$ replete** |
| Observed | 2,3-DPG | Control depleted | Equal to control** Less than $CO_2$ depleted** | Greater than control (through ~21 days) Greater than $CO_2$ replete** |

[1]Ar/$CO_2$ purged and Ar/$CO_2$ stored.
[2]Ar purged and Ar stored.
**Unexpected results.

DPG was not maintained by the association with $O_2$-depleted hemoglobin as shown in the $CO_2$ replete anaerobic arm. DPG was maintained in the $CO_2$ depleted arm. After approximately day 21 DPG did fall along with pH. This DPG fall may be associated with pH, indicating that enzymes in the DPG synthesis pathway may be affected by pH. Therefore, to maintain DPG in anaerobic storage, removal of $CO_2$ before and during storage of RBC is required.

Accordingly, the present invention is a method for enhancing red blood cell quality and survival during storage by depleting a red blood cell sample of both oxygen and carbon dioxide; and transferring the oxygen- and carbon dioxide-depleted red blood cell sample to an oxygen- and carbon dioxide impermeable environment. For the purposes of this invention, a red blood cell sample refers to whole blood; anti-coagulated whole blood (AWB); packed red cells obtained from AWB; and red cells separated from plasma and resuspended in physiological fluid. A red blood cell sample is typically supplied in a source container and can include any treated or untreated fluid from a living organism that contains red blood cells, particularly blood, including whole blood, warm or cold blood, and fresh blood; treated blood, such as blood diluted with a physiological solution, including but not limited to saline, nutrient, and/or anticoagulant solutions; analogous blood products derived from blood or a blood component. The red blood cell sample may include leukocytes, may be treated to remove leukocytes, may be treated with gamma or X-ray irradiation, washed, or treated to reduce or eliminate pathogens.

Depletion of both oxygen and carbon dioxide from the red blood cell sample can be achieved using any technique or combination of techniques described herein. For example, the instant method can employ gas purging and/or selective removal of $O_2$ and/or $CO_2$ with, e.g., a gas permeable membrane, an $O_2$ and/or $CO_2$ adsorbent, a molecular imprinted polymer, or a combination thereof. Techniques for purging blood via gas exchange with an inert gas such as argon are well-known and routinely practiced in the art. Gas permeable membranes have also been developed for removing $O_2$ and/or $CO_2$ from a liquid. Typically, the membranes are formed into hollow fibers and packaged in membrane modules, wherein the rate of gas transfer across the membrane is proportional to the gas permeability coefficient, the membrane surface area, the trans-membrane gas partial pressure difference, and inversely proportional to the membrane thickness. Exemplary gas permeable membrane modules of use in depleting oxygen and/or carbon dioxide are available from commercial sources. For example, PermSelect® Silicone Hollow Fiber Membranes, available from MedArray Inc. (Ann Arbor, Mich.); and Liqui-Cel® Membrane Contactors, available from Membrana-Charlotte (Charlotte, N.C.), are marketed for use in depleting oxygen and carbon dioxide from liquids in pharmaceutical and medical applications.

"Adsorbent" for the present purposes refers to a porous solid, particulate material or mixture of materials, which selectively admits and retains within its pores (or adsorbs) $O_2$ and/or $CO_2$ from a liquid. Suitable adsorbents for use in the present method are those having good selectivity for $O_2$ and/or $CO_2$ over other constituents (e.g., $N_2$), good kinetics, high durability, good chemical compatibility, and reasonably low cost. For example, molecular sieves are materials whose atoms are arranged in a lattice or framework in such a way that a large number of interconnected uniformly sized pores exist. The pores generally only admit molecules of a size about equal to or smaller than that of the pores. Molecular sieves, thus, can be used to adsorb and separate or screen molecules based on their size with respect to the pores. One class of molecular sieves is zeolites, which have been shown to exhibit exceptional selective capture and storage of $CO_2$. Zeolites are hydrated silicates of aluminum. As such, zeolites, on account of their chemical composition, are part of a broader class of adsorbents called aluminosilicates. Other molecular sieves are formed from aluminophosphates, called $ALPO_4$'S, titanosilicates, metalloaluminates, etc. Zeolites can be naturally occurring or artificial. Activated alumina, activated carbon, and silica gel are other broad classes of adsorbents that could be used to capture $CO_2$. In some embodiments, the adsorbents are attached to a substrate (e.g., a bead, pellet, granule or particle) to facilitate contact with and removal of the adsorbents from the RBC.

A molecular imprinted polymer (MIP) is a polymer formed in the presence of a molecule that is extracted afterwards, thus leaving complementary cavities behind. These polymers show a chemical affinity for the original molecule and are of use in sensing and separation methods. For example, metal complexing imprinted polymers have been prepared for gas molecules such as NO, CO, $CO_2$ and oxygen, wherein the imprinted cavities in the polymer matrices were sized to the appropriate gas molecules used as the template. Moreover, copolymerization of these metal complexes into organic hosts such as porous methacrylate polymers has been shown to provide a substrate for binding gaseous molecules such as CO. Accordingly, molecular imprinted polymers in a bead, pellet, granule or particle format can be used in removal of $CO_2$ and oxygen in the instant method.

As exemplified herein, gas purging can achieve a $pCO_2$ of about 5 mmHg and a $pO_2$ of about 10 mmHg. Accordingly, in particular embodiments, the oxygen- and carbon dioxide-depleted red blood cell sample of the invention has a $pCO_2$ of less than or equal to about 5 mmHg and a $pO_2$ of less than or equal to about 10 mmHg. Alternatively, in so far as gas permeable membranes can deplete the oxygen in a liquid to a level of at least 1 ppb and $CO_2$ to a level of at least 1 ppm, other embodiments of this invention include depleting oxygen and carbon dioxide in the red blood cell sample to at least 1 ppb and 1 ppm, respectively. As is routine in the art, a $pO_2$ needle probe, or $pO_2$ and $pCO_2$ microelectrode can be used to measure oxygen and carbon dioxide levels in the oxygen- and carbon dioxide-depleted red blood cell sample.

Once the red blood cell sample is depleted of both oxygen and carbon, the red blood cell sample is transferred to an oxygen- and carbon dioxide-impermeable environment for storage. As used herein, an oxygen- and carbon dioxide-impermeable environment is a storage container or storage container system that is impermeable to oxygen and carbon dioxide. In accordance with the present invention, an oxygen- and carbon dioxide-impermeable storage container is a container, pouch, bag, or bottle that is constructed of a material compatible with a biological fluid, such as whole blood or a blood component and is capable of withstanding centrifugation and sterilization. Such containers are known in the art and include, e.g., for example, blood collection and satellite bags. Storage containers of use in the instant method can be made of plasticized polyvinyl chloride, e.g., PVC plasticized with dioctylphthalate, diethylhexylphthalate, or trioctyltrimellitate. The bags may also be formed from polyolefin, polyurethane, polyester, and polycarbonate. In one embodiment, the storage container itself is constructed of an oxygen- and carbon dioxide-impermeable material. Impermeable materials are routinely used in the art and any suitable material can be used. Existing systems use oxygen- and carbon dioxide-impermeable receptacles composed of layers of ethylene vinyl alcohol copolymer and modified ethylene vinyl acetate copolymer, impermeable to oxygen and carbon dioxide ingress. In another embodiment, the storage container is a component of a storage container system that is impermeable to oxygen and carbon dioxide. Such systems include, but are not limited to, use of an oxygen- and carbon dioxide-impermeable over wrap or over bag which encloses the storage container.

To ensure that there is no ingress of oxygen or carbon dioxide into the sample during transfer, in particular embodiments, the oxygen- and carbon dioxide-depleted red blood cell sample is transferred to the storage container under positive pressure. Positive pressure is a pressure within a system that is greater than the environment that surrounds that system. Positive pressure can be attained by transferring the sample to the storage container in a closed system, e.g., via tubing between one or more of the source container, oxygen and carbon dioxide depletion apparatus, and storage container. Airtight, pressurized fluid delivery systems for facilitating positive fluid flow are known in the art. Transfer of the oxygen- and carbon dioxide-depleted red blood cell sample to the storage container can be achieved using various techniques including, but not limited to peristalsis, a siphon, or a combination thereof. By way of illustration, the red blood cell sample can be transferred via a tube from the source container to a gas permeable membrane module or molecular sieve device and subsequently to the source container via another tube, wherein the source container, membrane or sieve, and storage container are positioned in an inverted siphon configuration.

As used herein, tubing can be any conduit or means which provides fluid communication between containers, and is typically made from the same flexible material as is used for the containers, and is desirably oxygen- and carbon dioxide impermeable. The tubing may extend into the interior of the containers herein, and may be used as a siphon, for example. There may be a number of tubes providing fluid communication to any individual container, and the tubes may be oriented in a number of ways. A seal, valve, clamp, transfer leg closure, or the like can also be located in or on the tubing. It is intended that the present invention is not limited by the type of material used to construct the containers or the conduit which connects the containers.

Once transferred to the storage container, the red blood cell sample can be stored under aerobic or anaerobic conditions, i.e., conditions of low or no oxygen. Desirably the sample is stored between 1° C. and 6° C. to further enhance the survival of the red blood cells.

Compared to a red blood cell sample not prepared in accordance with the present method, the quality and survival of the red blood cell sample of the invention is enhanced. In this respect, the red blood cells of the instant sample exhibit less than 0.7%, hemolysis at 9 weeks, less than 0.3% hemolysis at 7 weeks, and less than 0.2% hemolysis at 3 weeks after treatment by the instant method. The determination of red blood cell hemolysis is routinely practiced in the art and any suitable method can be employed.

Moreover, when the instant method is carried out in the presence of acidified additive solution (i.e., an additive solution of between pH 5.5 and 7.0, or more desirably between 6.25 and 6.75), 2,3-DPG levels of the RBCs are maintained at higher levels than controls (e.g., a sample wherein carbon dioxide is not depleted); i.e., 2,3-DPG levels are approximately 60% higher than controls at 3 weeks. 2,3-DPG levels are routinely measured and any suitable method can be used to determined whether 2,3-DPG levels of a red blood cell sample produced by the instant method are being maintained above control samples.

By maintaining 2,3-DPG levels within the RBC, the RBC can provide better oxygen transfer to tissues when the RBC is transfused to patients. This improvement can also provide improved recovery of transfused RBC in patients and study subjects. The present finding provides a mechanism to increase the acceptable storage time of RBC for transfusion or other purposes. In this respect, the red blood cells of the red blood cell sample can be used, e.g., in a transfusion, for at least 4, 5, 6, 7, 8, or 9 weeks after treatment by the instant method.

Example 1

Materials and Methods

It was determined whether removal of $CO_2$ during oxygen depletion by gas exchange affects RBC in a significant manner during subsequent anaerobic storage. Using a three-way, split-unit study, 12 units (6 units with AS3 and 6 with OFAS3) were evaluated, which compared anaerobically stored RBC units with oxygen depletion accomplished using 100% Ar vs. a 95% Ar/5% $CO_2$ gas mixture. As a control, one of the three-way split units was stored conventionally in AS3 (also known as NUTRICEL, Pall Corp.) (Hess, et al. (2000) supra) additive or the OFAS3 (Dumont, et al. (2009) supra).

The primary endpoints of this study included the weekly determination of biochemical parameters such as hemoglobin, extracellular pH (pHe), internal pH (pHi), partial pressure of carbon dioxide ($pCO_2$), partial pressure of oxygen ($pO_2$), hematocrit, ATP, 2,3-DPG levels, supernatant hemoglobin, glucose, lactate, Na+, K+ and % hemolysis carried out during nine weeks of refrigerated storage.

Preparation of Red Cells for Storage.

Each unit of blood (500 mL) was collected into LEU-KOTRAP RC Whole Blood Collection, Filtration and Storage System with Pall RC2D Filter containing CP2D in the primary bag. The blood was held at room temperature (RT) for 30 minutes, prior to centrifugation. Subsequently, the blood was centrifuged at 2,000×g for 3 minutes ('soft spin'-slow stop and no brake), and the supernatant (platelet-rich plasma fraction) was expressed into the attached satellite bag and discarded. After centrifugation, additive solution (100 mL of AS-3 or 200 mL of OFAS3) was added to the unit of packed red blood cells (pRBC). When OFA was being added, the pre-prepared bag was sterilely docked to the pRBC collection bag set. The pRBC unit was mixed very well with the "blood vortex" method-opposite end rotation. Subsequently, the pRBC unit in additive solution was leukoreduced at room temperature using the attached RC2D filter. The pRBC unit was divided equally into three 600 mL bags by mass for the following treatment: Control, 100% Ar, and 5% $CO_2$/Ar. Before transferring the pRBC unit into the three 150 mL bags, each bag was purged with the appropriate gas: control (none), 100% Ar, or 5% $CO_2$/Ar. Upon transfer, the control bag was mixed for 70 minutes on an agitator at room temperature. For the 100% Ar bag and 5% $CO_2$/Ar bag, the RBC was depleted of oxygen as described herein. Each 150 mL bag was sampled by sterilely docking a plasma transfer set (syringe with tubing). After removal of the 9 mL of pRBC for testing, the bag was purged completely of "gas head" with a syringe. Each unit was placed within a temperature monitored blood storage refrigerator which maintained the temperature at 4° C. On a weekly basis for 9 weeks, each unit was mixed and sampled.

Oxygen Depletion with 100% Argon.

Argon was filter sterilized through a 0.22 micron hydrophilic filter and introduced into the pRBC bag. Care was taken not to pressurize the bag at this point. The bag was gently mixed with a rocking motion for 10 minutes at 21-25° C., then the gas was gently expressed through the filter using a vacuum. Flushing with Argon gas, gentle mixing, and gas phase expression was repeated six additional times at 21-25° C. (for a total of seven times). After the final exchange, a 9 mL sample was taken from the bag. Analysis of oxygen and carbon dioxide levels in the depleted RBC indicated that the $pCO_2$ was about 5 mmHg and the $pO_2$ was about 10 mmHg (at a temperature of from 21-25° C. The bags were stored in a gas-tight canister containing a Pd catalyst (DIFCO). The vacuum was set at ~−0.7 bar (1 bar=0.987 standard atmosphere). The canister was filled with Ar to ~0.7 bar. The canister was evacuated to ~−0.7 bar, and filled with 10% $H_2$/90% Ar gas mixture to +0.3 bar. Hydrogen and the Pd catalyst form a fully functional oxygen scavenging system. The canister was placed within a temperature monitored blood storage refrigerator, which maintained 4° C.

Oxygen Depletion with 95% Argon/5% $CO_2$.

A gas mixture of Argon/5% $CO_2$ gas was filter sterilized through a 0.22 micron hydrophilic filter and introduced into the bag. Care was taken not to pressurize the bag at this point. The bag was gently mixed with a rocking motion for 10 minutes at 21-25° C., and the gas was gently expressed through the filter using a vacuum. Flushing with the gas mixture, gentle mixing, and gas phase expression, were repeated six additional times at 21-25° C. (for a total of seven times). After the final exchange, a 9 mL sample was taken from the bag. The bags were stored in a gas-tight canister containing a Pd catalyst. The vacuum was set at ~−0.7 bar. The canister was filled with Ar to ~0.7 bar. The canister was evacuated to ~−0.7 bar, and filled with 5% $CO_2$/10% $H_2$/90% Ar gas mixture to +0.3 bar. The canister was placed within a temperature monitored blood storage refrigerator, which maintained 4° C.

Example 2

$CO_2$ Depletion Provides a Metabolic Advantage for Stored RBC

The instant analysis was a matched three arm study including a control sample, a sample depleted of $O_2$ and $CO_2$ with Ar, and a sample depleted of $O_2$ with 95% Ar/5% $CO_2$. Whole blood was collected into CP2D (Pall), centrifuged 2000×g for 3 minutes, plasma removed, and additive solution AS-3 (Nutricel, Pall), or experimental OFAS3 added. The unit was evenly divided into three 600 mL bags. Two bags were gas exchanged with Ar or Ar/$CO_2$, transferred to 150 mL PVC bags and stored at 1-6° C. in anaerobic cylinders with Ar/$H_2$ or Ar/$H_2$/$CO_2$. One control bag was treated in the same manner without a gas exchange and stored at 1-6° C. in ambient air. Bags were sampled weekly for up to 9 weeks and a panel of in vitro tests were conducted on each sample including intra- and extra-cellular pH (pHi, pHe).

As shown in Table 2, purging with Ar resulted in alkalization of the RBC and upregulation of glycolysis compared to control. pH and lactate of Ar/$CO_2$-purged RBC were equivalent to aerobically stored controls (p>0.5, days 0-21). ATP levels were higher in Ar/$CO_2$ (p<0.0001). DPG was maintained beyond 2 weeks in the Ar-purged arm only (p<0.0001). Surprisingly, DPG was lost at the same rate in both control and Ar/$CO_2$ arms (p=0.6). Hemolysis was low in all arms, but may have been influenced by the weekly mixing.

By reducing carbon dioxide and oxygen in the red blood cell ATP levels were maintained at higher levels for nine weeks relative to ATP levels in a red blood cell sample in which neither oxygen nor carbon dioxide were depleted. 2,3-DPG levels were maintained at a higher level for three weeks than 2,3-DPG levels in a red blood cell sample in which neither oxygen nor carbon dioxide were depleted. Oxygen depletion has a positive impact on ATP levels in red blood cell samples and carbon dioxide depletion has a positive impact on 2.3-DGP levels. Optimal results are achieved when both oxygen and carbon dioxide are depleted.

Although the present disclosure describes in detail certain embodiments, it is understood that variations and modifications exist known to those skilled in the art that are within the disclosure. Accordingly, the present disclosure is intended to encompass all such alternatives, modifications and variations that are within the scope of the disclosure as set forth in the disclosure.

TABLE 2

| Arm | Day | pHi (22° C.) | ATP (µmol/ gHb) | 2,3-DPG (µmol/ gHb) | Lactate (mmol/ gHb) | Glucose (mmol/ gHb) | Hemolysis (%) |
|---|---|---|---|---|---|---|---|
| Control | 0 | 7.11 ± 0.04 | 4.1 ± 0.7 | 12.2 ± 1.8 | 0.01 ± 0 | 0.38 ± 0.13 | 0.20 ± 0.04 |
|  | 21 | 6.77 ± 0.05 | 4.3 ± 1.0 | 0.2 ± 0.2 | 0.11 ± 0.02 | 0.30 ± 0.13 | 0.20 ± 0.06 |
|  | 42 | 6.56 ± 0.06 | 3.1 ± 0.8 | 0.2 ± 0.1 | 0.16 ± 0.02 | 0.27 ± 0.13 | 0.30 ± 0.10 |
|  | 63 | 6.44 ± 0.07 | 2.1 ± 0.6 | 0.3 ± 0.2 | 0.2 ± 0.02 | 0.26 ± 0.13 | 0.53 ± 0.20 |
| Ar/$CO_2$ | 0 | 7.14 ± 0.03 | 4.6 ± 0.7 | 12.2 ± 1.8 | 0.02 ± 0 | 0.38 ± 0.12 | 0.17 ± 0.04 |
|  | 21 | 6.76 ± 0.04 | 5.5 ± 1.3 | 0.2 ± 0.2 | 0.1 ± 0.02 | 0.33 ± 0.13 | 0.19 ± 0.08 |
|  | 42 | 6.58 ± 0.05 | 4.0 ± 1.3 | 0.1 ± 0.0 | 0.15 ± 0.03 | 0.30 ± 0.13 | 0.32 ± 0.11 |
|  | 63 | 6.51 ± 0.06 | 2.4 ± 1.0 | 0.1 ± 0.0 | 0.19 ± 0.03 | 0.28 ± 0.13 | 0.61 ± 0.26 |

TABLE 2-continued

| Arm | Day | pHi (22° C.) | ATP (μmol/ gHb) | 2,3-DPG (μmol/ gHb) | Lactate (mmol/ gHb) | Glucose (mmol/ gHb) | Hemol- ysis (%) |
|---|---|---|---|---|---|---|---|
| Ar | 0 | 7.38 ± 0.06 | 4.6 ± 0.8 | 14.3 ± 1.6 | 0.02 ± 0 | 0.38 ± 0.13 | 0.18 ± 0.05 |
|  | 21 | 6.67 ± 0.04 | 4.7 ± 0.9 | 6.2 ± 3.0 | 0.16 ± 0.02 | 0.33 ± 0.14 | 0.19 ± 0.04 |
|  | 42 | 6.42 ± 0.06 | 3.3 ± 0.9 | 0.4 ± 0.2 | 0.21 ± 0.02 | 0.32 ± 0.13 | 0.28 ± 0.08 |
|  | 63 | 6.31 ± 0.09 | 1.8 ± 0.9 | 0.4 ± 0.2 | 0.24 ± 0.02 | 0.3 ± 0.14 | 0.64 ± 0.35 | mean ± sd

The results of this analysis indicated that the addition of 5% $CO_2$ to the purging gas prevented $CO_2$ loss with an equivalent starting pHi and pHe to control bags. Maintenance of ATP in the Ar/$CO_2$ arm demonstrated that ATP production was not solely a function of the pH effect on glycolysis. $CO_2$ in anaerobic storage prevented the maintenance of DPG, and DPG appeared to be pH dependent. Therefore, $CO_2$ as well as $O_2$ depletion provided metabolic advantage for stored RBC.

What is claimed is:

1. A method for enhancing red blood cell quality and survival during storage comprising
   (a) depleting a red blood cell sample of leukocytes;
   (b) depleting said leukocyte depleted red blood sample of platelets;
   (c) adding an additive solution having a pH ranging from 5.5 to 7.0;
   (d) depleting said leukoreduced and platelet reduced red blood cell sample of both oxygen and carbon dioxide prior to storage, wherein carbon dioxide is depleted to a level of 5 mmHg at 21-25° C.; and
   (e) transferring the leukocyte, platelet and oxygen- and carbon dioxide-depleted red blood cell sample to an oxygen- and carbon dioxide-impermeable environment for storage, wherein said red blood cell sample has an acidic pH,
   thereby enhancing red blood cell quality and survival during storage.

2. The method of claim 1, wherein 2,3-diphosphoglycerate (2,3-DPG) acid levels are maintained for at least two weeks.

3. The method of claim 1, wherein the red blood cell sample is stored for at least three weeks.

4. The method of claim 3, wherein the red blood cells exhibit less than 0.2% hemolysis.

5. The method of claim 1, wherein the red blood cells sample is stored for at least seven weeks.

6. The method of claim 5, wherein the red blood cells exhibit less than 0.3% hemolysis.

7. The method of claim 1, wherein the red blood cells sample is stored for at least nine weeks.

8. The method of claim 7, wherein the red blood cells exhibit less than 0.7% hemolysis.

9. The method of claim 1, wherein the red blood cell sample is depleted of oxygen to a level of approximately 10 mmHg at 21-25° C.

10. The method of claim 1, wherein said additive solution has a pH ranging from 6.25 to 6.75.

11. The method of claim 1, wherein the oxygen- and carbon dioxide-impermeable environment for storage is between 1° C. and 6° C.

12. The method of claim 1, wherein the red blood cell sample is selected from the group consisting of whole blood, anti-coagulated whole blood, packed red cells and red cells separated from plasma.

13. A method for enhancing red blood cell quality and survival during storage comprising
   (a) reducing oxygen and carbon dioxide in a red blood cell sample comprising an acidified additive solution prior to storage; and
   (b) storing the oxygen and carbon dioxide reduced red blood cell sample in an oxygen and carbon dioxide-impermeable storage environment, wherein said red blood cell sample has an acidic pH,
   wherein adenosine triphosphate (ATP) and 2,3-diphosphoglycerate (2,3-DPG) levels are optimized during storage in the oxygen- and carbon dioxide-impermeable storage environment.

14. The method of claim 13, wherein the red blood cell sample is depleted of oxygen to a level of approximately 10 mmHg at 21-25° C.

15. The method of claim 13, wherein the red blood cell sample is depleted of carbon dioxide to a level of 5 mmHg at 21-25° C.

16. The method of claim 13, wherein reducing carbon dioxide in the red blood cell sample elevated 2,3-DPG levels relative to a red blood cell sample in which carbon dioxide was not depleted.

17. The method of claim 13, wherein reducing carbon dioxide and oxygen in the red blood cell sample maintains ATP levels higher for a nine week period than ATP levels in a red blood cell sample in which neither oxygen nor carbon dioxide are depleted and maintains 2,3-DPG levels higher for three weeks than 2,3-DPG levels in a red blood cell sample in which neither oxygen nor carbon dioxide are depleted.

* * * * *